(12) United States Patent
Chen

(10) Patent No.: US 11,420,111 B2
(45) Date of Patent: Aug. 23, 2022

(54) LARGE-SCREEN VR INTEGRATED GAME MACHINE

(71) Applicant: VR LEO USA, INC., Los Angeles, CA (US)

(72) Inventor: Xiuchao Chen, Shanghai (CN)

(73) Assignee: VR LEO USA, INC, Los Angeles, CA (US)

( * ) Notice: Subject to any disclaimer, the term of this patent is extended or adjusted under 35 U.S.C. 154(b) by 119 days.

(21) Appl. No.: 16/822,941

(22) Filed: Mar. 18, 2020

(65) Prior Publication Data

US 2020/0298107 A1    Sep. 24, 2020

(30) Foreign Application Priority Data

Mar. 21, 2019  (CN) .......................... 201920364425.9

(51) Int. Cl.
| | |
|---|---|
| *G02B 27/01* | (2006.01) |
| *A63F 13/27* | (2014.01) |
| *A63F 13/98* | (2014.01) |
| *A63F 13/2145* | (2014.01) |
| *G06F 3/01* | (2006.01) |

(52) U.S. Cl.
CPC .......... *A63F 13/27* (2014.09); *A63F 13/2145* (2014.09); *A63F 13/98* (2014.09); *G02B 27/0172* (2013.01); *G06F 3/011* (2013.01); *A63F 2300/1043* (2013.01); *A63F 2300/1075* (2013.01); *A63F 2300/8023* (2013.01); *A63F 2300/8082* (2013.01)

(58) Field of Classification Search
CPC .......... A63F 13/02; A63F 13/27; A63F 13/90; A63F 13/98; A63F 2300/1043; A63F 2300/1075; A63F 2300/8082; G07F 17/3209; G07F 17/3211; G07F 17/3216; G06F 3/011; A61L 2/10; G02B 2027/0169; G02B 2027/0176; G02B 2027/0181
See application file for complete search history.

(56) References Cited

U.S. PATENT DOCUMENTS

2019/0227328 A1*  7/2019  Coatney ................ G06T 19/006

* cited by examiner

*Primary Examiner* — Lawrence S Galka
(74) *Attorney, Agent, or Firm* — M.J. Ram and Associates

(57) ABSTRACT

A large-screen VR integrated game machine comprises an upper assembly moveably attached to a lower assembly. A VR head mounted display retracting device positioned within the interior of the upper display, comprises a power transmission system, an electrical control system and a pulley system. The VR integrated game machine moveable upper assembly provides a folding structure that allows easier maintenance and upgrades of the equipment under unattended operation. Because the game machine is foldable the height can be shortened to alleviate transportation difficulties and set up at an operation site.

12 Claims, 4 Drawing Sheets

LARGE-SCREEN VR INTEGRATED GAME MACHINE

This application claims benefit of Chinese Application No. 201920364425.9 filed Mar. 21, 2019.

TECHNICAL FIELD

The present description relates to the technical field of integrated game machines, and in particular to a large-screen virtual reality (VR) integrated game machine.

BACKGROUND ART

A large-screen VR integrated game machine is a gaming device that can provide a virtual reality gaming experience. A VR integrated game machine as described herein a type of amusement equipment that integrates a head mounted display for playing the VR game, a game control handle, a computer based PC host device for viewing and playing VR games, VR games installed in the PC host device, and a gaming platform. A user can enjoy VR games through the VR integrated game machine. However, the existing integrated game machines have deficiencies in many areas, including their transmission mechanism, the VR game control handle, and the manner in which the various parts of the equipment are combined. More specifically:
1. The existing VR integrated game machines have many separate modules, the installation of these modules is thus difficult, and the complex structure of the assembled modules makes it difficult for maintenance;
2. The existing VR integrated game machines are large in size, occupies a large space, and equipment height is not adjustable, which not only results in inconvenience in transportation, but also has specific height requirements for the operation site;
3. The VR control handle has no mounting structure and thus may be placed anywhere by users because there is no fixed mounting position; and
4. Because of the external machine structure the existing devices have problems in transportation and maintenance.

SUMMARY

To solve the deficiencies in the existing technology, the present embodiments provide a large-screen VR integrated game machine which can provide VR game machine sharing and unattended operation. In addition, the external parts of the equipment have a foldable design. Accordingly, its structure is convenient for maintenance and upgrade. Moreover, the folding structure facilitates transportation.

The technical solutions employed by the present utility model to solve the technical problems are as follows:

A large-screen VR integrated game machine comprises an upper assembly and a lower assembly, characterized in that the upper assembly is disposed on a top portion of the lower assembly. A VR head mounted display retracting device is fixedly connected to an interior of the upper display. The VR head mounted display retracting device comprises an installation protection bracket, a power transmission system, an electrical control system, and a pulley system. The power transmission system is disposed within the installation protection bracket, the electrical control system is fixedly connected to an outer wall of the installation protection bracket, the pulley system is movably connected to the power transmission system, and the electrical control system is electrically connected to the power transmission system through a wire.

Preferably, the upper assembly comprises an upper assembly casing, wherein a lower surface of the upper assembly casing is fixedly connected with an upper assembly folding device. A side of the upper assembly folding device distanced from the upper assembly casing is fixedly connected with an upper assembly flip plate and a front surface of the upper assembly folding device is fixedly connected with a folding device access door. The VR head mounted display retracting device is fixedly connected to an interior of the upper assembly casing, an upper surface of the upper assembly casing is fixedly connected with a retracting device access door and one end of the upper assembly casing distanced from the upper assembly folding device is fixedly connected with a head mounted display protection cover. A lower surface of the head mounted display protection cover is fixedly connected with an ultraviolet disinfection light. A lower surface of the upper assembly flip plate is fixedly connected with the lower assembly. The head mounted display protection cover and the VR head mounted display retracting device are connected together via a fastener and further fixedly connected to the upper assembly flip plate via a hinge.

Preferably, the lower assembly comprises a lower assembly casing with an outer wall of the lower assembly casing having an external power supply socket and a leakage protection circuit breaker where the external power supply socket is disposed on a front surface of the leakage protection circuit breaker. The outer wall of the lower assembly casing is connected with a folding device operation switch disposed on a rear surface of the leakage protection circuit breaker. The outer wall of the lower assembly case is also provided with an external network port. A right side of the outer wall lower assembly casing is movably connected to a power supply board protection door disposed on a right side of the external power supply socket. An audio device is fixedly connected to an interior of the lower assembly casing. The outer wall of the lower assembly casing is movably connected to a lower assembly access door and a PC host is fixedly connected to a top portion of an inner wall of the lower assembly casing. An upper surface of the lower assembly casing is fixedly connected with a cooling fan and the outer wall of the lower assembly casing is provided with a VR control handle access port. A liquid crystal display is movably connected to an interior of the lower assembly casing and a touch screen is fixedly connected to the outer wall on the left side of the liquid crystal display. A display installation protection frame is fixedly connected to the outer wall of the left side of the lower assembly casing with a decorative light set is fixedly connected to the outer wall of the left side of the lower assembly casing, the decorative light set is disposed below the display installation protection frame. A lower surface of the lower assembly casing has a universal wheel fixedly connected thereto.

Preferably, the installation protection bracket has a motor mounting base and a redirecting sprocket mounting base and an outer wall of the motor mounting base is fixedly connected with a protection cover. An inner wall of the protection cover is movably connected to an outer wall of the motor mounting base and an outer wall of the redirecting sprocket mounting base.

Also preferably, the power transmission system comprises a motor with a driving sprocket fixedly connected to one end of an output shaft of the motor. An inner wall of the driving sprocket is movably connected with an inner friction plate and an outer friction plate, a lock nut is movably connected to an interior of the outer friction plate and a bead screw is movably connected to an outer wall of the outer friction plate. The driving sprocket is fixedly connected with a friction plate pressure plate through a fastener, a chain is movably connected to an outer wall of the driving sprocket, and a redirecting sprocket is movably connected to an interior of the chain.

Preferably, the electrical control system comprises a home limit switch with an outer wall of the home limit switch fixedly connected to an outer wall of the motor mounting base, and an outer wall of the redirecting sprocket mounting base is fixedly connected with a position limit switch.

Preferably, the pulley system comprises a linear bearing block set with an outer wall of the linear bearing block set fixedly connected with a bearing mounting base. A guide shaft is fixedly connected to an outer wall of the bearing mounting base with an outer wall of the guide shaft movably connected with a pulley. An outer wall of the linear bearing block set is fixedly connected with a connecting piece and an outer wall of the connecting piece is movably connected with an outer wall of the chain.

The present embodiments provide a large-screen VR integrated game machine, which has the following beneficial effects:

The present embodiment comprising a folding upper assembly and a lower assembly solves the problem of inconvenient maintenance and upgrades of the equipment under unattended conditions and ensures uninterrupted operation of the equipment. The capability to fold the upper assembly allows the height of the whole machine to be adjusted, thus addressing the problems of difficult transportation and unsatisfactory height of an operation site. By providing a VR head mounted display retracting device the head mounted display storage part can be retracted by itself, even after a sudden power failure, addressing the problem of the safety of the equipment under unattended conditions. By providing and controlling an ultraviolet disinfection light to irradiate the head mounted display, the head mounted display components can be sterilized and disinfected, which addresses the problem of a contaminated system and public health. At the same time, the large-sized liquid crystal display and touch screen are used to achieve an enjoyable experience of a VR games on a large screen, solving the design problem of integrating of large screens and VR equipment. The present embodiment has simple operation and is easy to use. The head mounted display provides for automatically storage and lowering. Also, the game control handle can be easily controlled. In this way, the present embodiment provides for unattended operation of shared VR game machines, the later operations become simpler and more efficient, the costs are reduced, and the wear rate of the equipment is greatly reduced.

DETAILED DESCRIPTION

The technical solutions of the present embodiments are described below in combination with reference to the drawings of the embodiments. Based on the embodiments described herein many other embodiments would be recognized by a person of ordinary skill in the art with which are also within the scope of protection of the present invention.

The structural composition of the present embodiment is described in detail below with reference to FIGS. 1 to 3 for detailed description.

Figure 1:
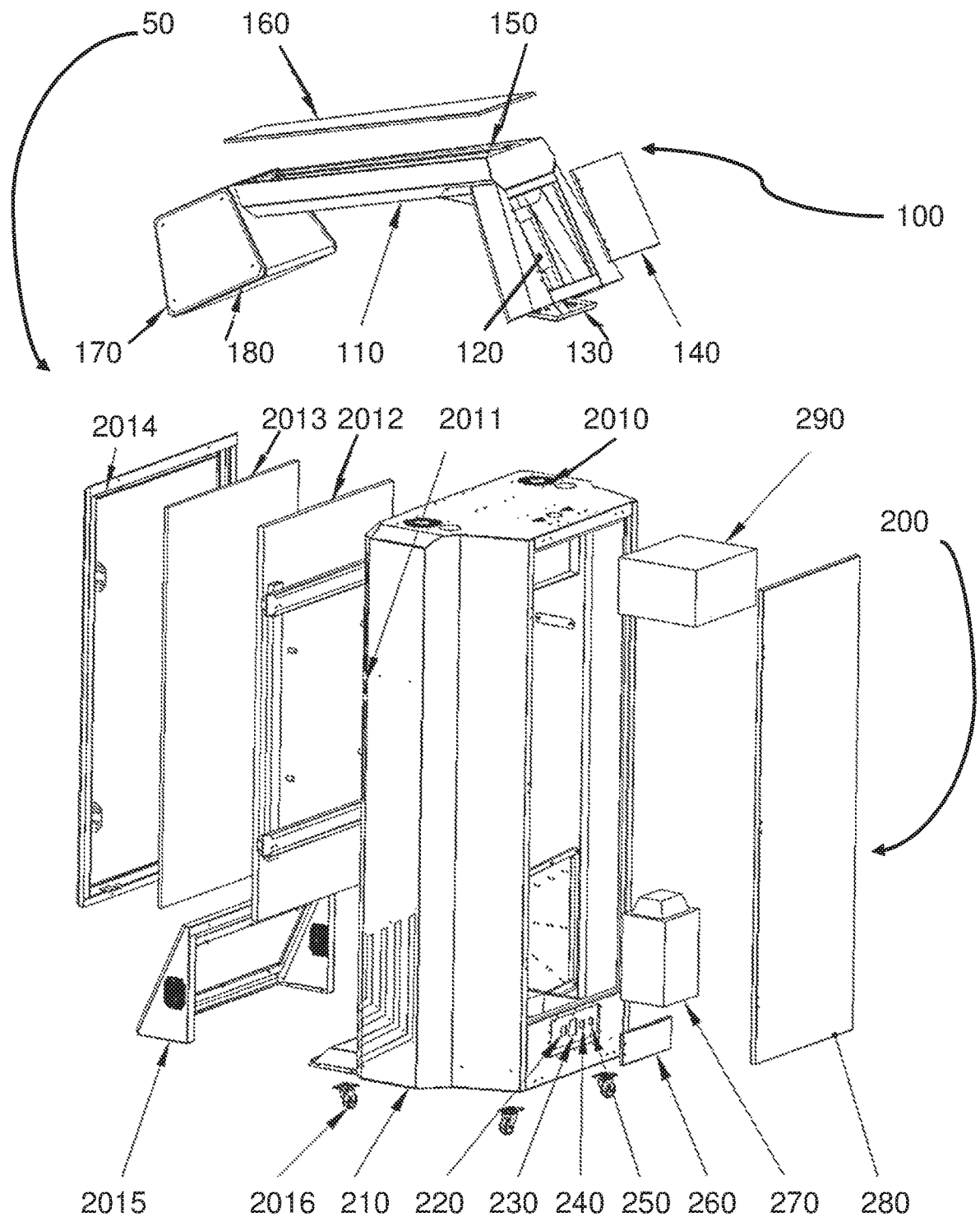
FIG. 1 is an exploded view of a structure of an embodiment incorporating features of the present invention.
Figure 2:
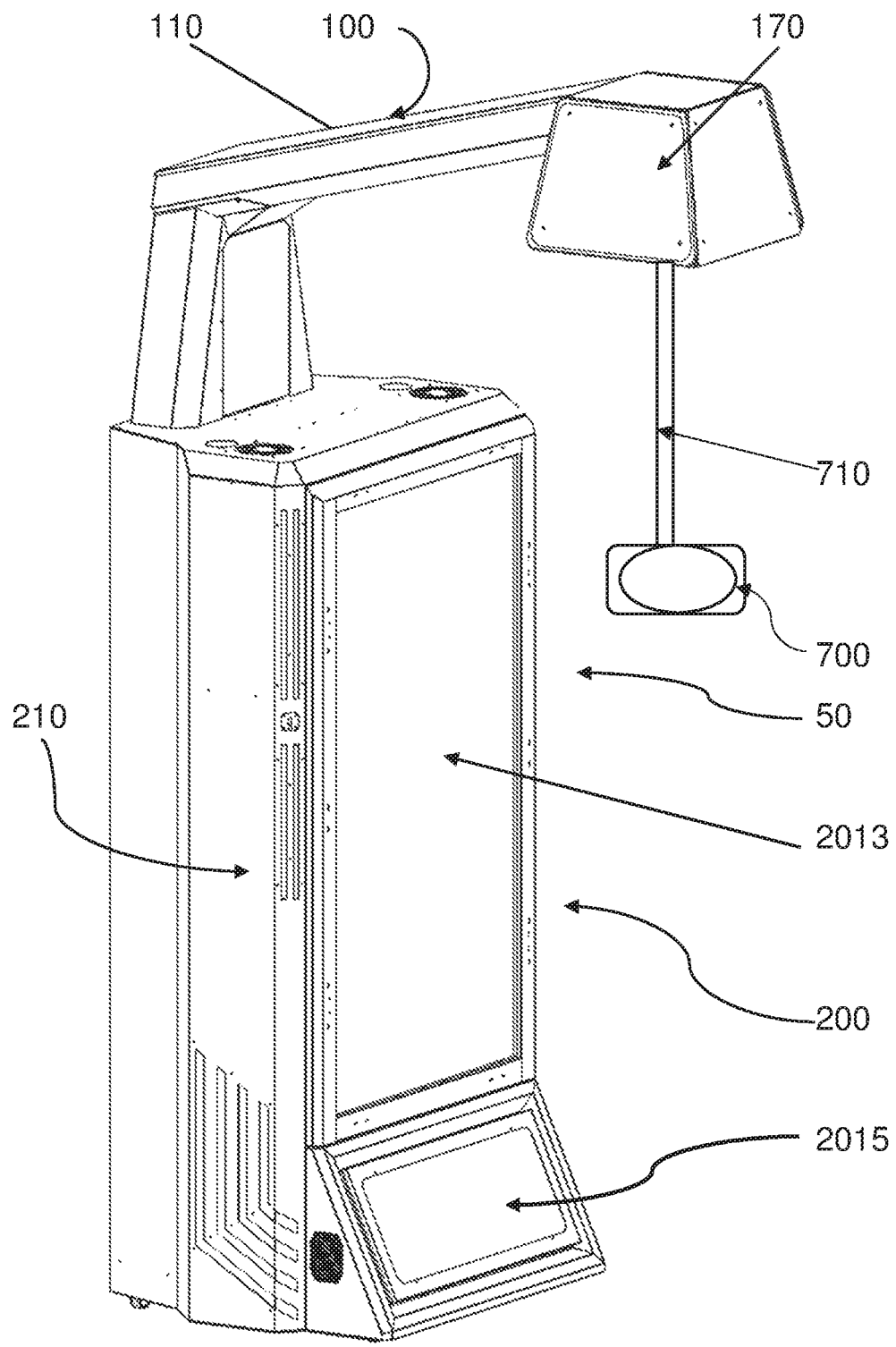
FIG. 2 is a perspective view of the embodiment of FIG. 1 also showing a cable and a head mounted VR display.
Figure 3:
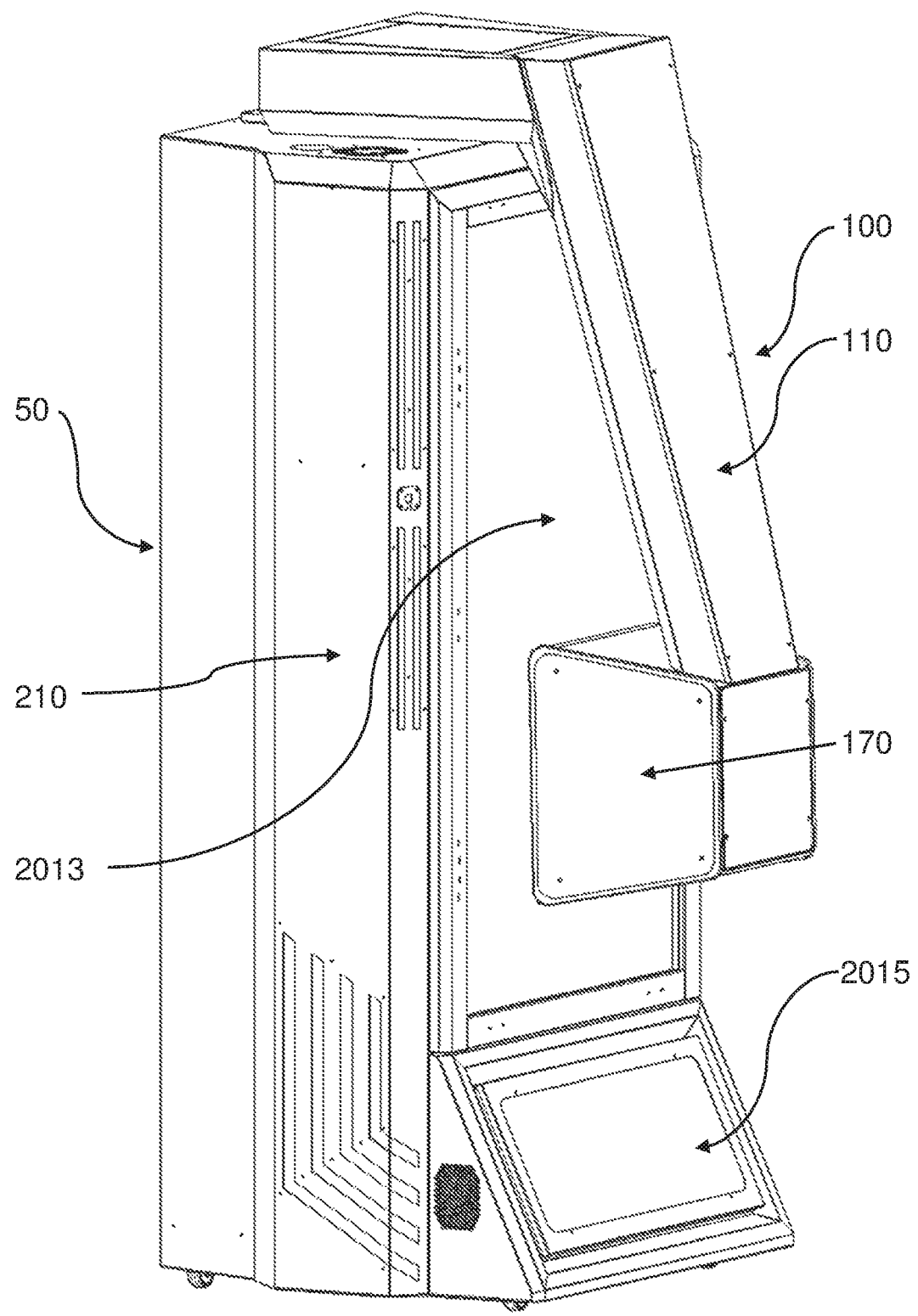
FIG. 3 is a view of the embodiment of FIG. 2 in a folded state such as for transportation.

As shown in FIGS. 1 to 3, the present embodiment of a large-screen VR integrated game machine 50 is composed of an upper assembly 100 and a lower assembly 200. The upper assembly 100 is a hollow structure composed of the upper assembly casing 110, the upper assembly folding device 120, the head mounted display protection cover 170 and the VR head mounted display retracting device 150 which are all connected together via fasteners.

The upper assembly 100 includes an upper assembly casing 110 and an upper assembly folding device 120. On the lower end of the upper assembly folding device 120 is an upper assembly flip plate 130. A folding device access door 140 is located on a face of the upper assembly folding device 120. Attached to an upper end of the upper assembly folding device 120 is a VR head mounted display retracting device 150 which has a retracting device access door 160. Located on an upper end of the VR head mounted display retracting device 150 is a head mounted display protection cover 170 which includes an ultraviolet disinfection light 180. The bottom portion of the entire hollow structure upper assembly 100 is connected to the upper assembly flip plate 130 through a hinge. In addition, two ends of a variable distance electric push rod (not shown) are hinged to the upper assembly flip plate 130 and the upper assembly casing 110 respectively to form a crank rocker mechanism, to provide flipping and folding of the components. The folding device access door 140 and the retracting device access door 160 are openable for easy maintenance. Moreover, the entire upper assembly 100 is connected to the lower assembly 200 through the upper assembly flip plate 130 using fasteners.

As shown in FIG. 1 and as further described below, the lower assembly 200 comprises a lower assembly casing 210 which includes an external power supply socket 220, a leakage protection circuit breaker 230, a folding device operation switch 240, an external network port 250, a power supply board protection door 260, a speaker 270, a lower assembly access door 280, a PC host 290, a cooling fan 2010, a VR control handle access port 2011, a liquid crystal display 2012, a touch screen 2013, a display installation protection frame 2014, a decorative light set 2015 and four wheels 2016.

The lower assembly casing 2010, which surrounds the lower assembly 200, has a liquid crystal display 2102 embedded therein. The liquid crystal display 2012 is equipped with a touch screen 2013 on an outer side thereof, the touch screen 2013 being surrounded by a display installation protection frame 2014. The decorative light set 2015 is mounted on a front lower side to protect and decorate the touch screen 2013. The lower assembly casing 210 has an openable casing back plate 280 on a rear side thereof. The PC host 290 and the speaker 270 are installed inside the lower assembly casing 210. The cooling fan 2010 is located on an upper left side of the casing; the PC host 290 is located at an upper middle position of the casing, and the speaker 270 is placed on the lower part of the casing. The power supply and protection devices for all components are installed below the lower assembly access door 280, which is further connected to an external power supply via the external power supply socket 220. The leakage protection circuit breaker 230 is provided to ensure staff safety. The folding device operation switch 240 controls the folding and flipping of the upper assembly 200. The external network port 250 provides a wired network connection to external devices. There is a power supply board protection door 260 on an outer side thereof to prevent potential damages caused by mis-operation by staff or other people. The VR control handle cabling (not shown) enters the lower assembly casing 210 through the VR control handle access port 2011 and is then connected to the PC host 290. The four wheels 2016 are installed below the lower assembly casing 210, to facilitate short distance movement of the equipment.

The structural composition of the VR head mounted display retracting device of the present utility model are further described in detail below with reference to FIG. 4.

Figure 4:
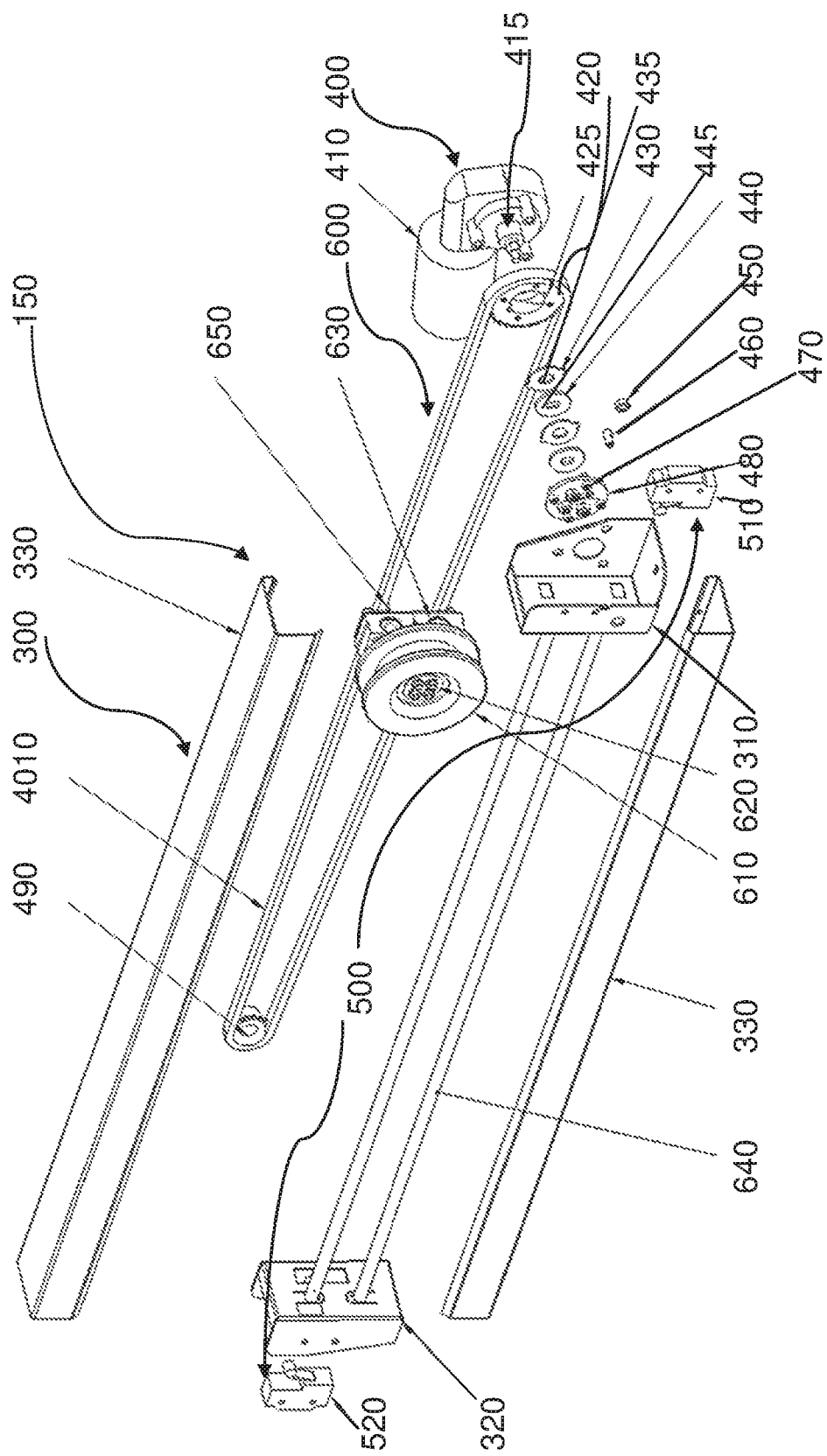
FIG. 4 is an exploded view of the structure of a VR head mounted display retracting device for use with the embodiment of FIGS. 1-3.

As shown in FIG. 4, the VR head mounted display retracting device 150 includes an installation protection bracket 300, a power transmission system 400, an electrical control system 500 and a pulley system 600. The power transmission system 400 is disposed within the installation protection bracket 300, the electrical control system 500 is fixedly connected to an outer wall of the installation protection bracket 300, the pulley system 600 is movably connected to the power transmission system 400, the electrical control system 500 is electrically connected to the power transmission system 400 through a wire.

The motor mounting base 310, the redirecting sprocket mounting base 320 and the protection cover 330 are attached, preferably by welding, to form the entire installation protection bracket 300. In addition, the home limit switch 510 is installed on the motor mounting base 310 and the position limit switch 520 is installed on the redirecting sprocket mounting base 320. The pulley 610 is fixed on the linear bearing block set 630 through a pulley mounting base 620, which is restricted by two guide shafts 640 installed on the installation protection bracket 300 to thus enabling movement back and forth on the guide shafts 640. The connecting piece 650 and the linear bearing seat 630 are connected by fasteners. These components constitute the pulley system 600.

The power transmission system 400 is mainly composed of a motor 410, a chain 4010, a redirecting sprocket 490, a driving sprocket 420, an outer friction plate 430, an inner friction plate 440, and a friction plate pressure plate 480. A central hole in the inner friction plate 440 limits an output (output) shaft 415 of the motor 410 via a limiting slot 445. An outer ring is in contact with the driving sprocket 420, and can rotate freely inside. An outer flange 435 of the outer friction plate 430 is embedded into a slot 425 in a central hole of driving sprocket 420. In addition, the central hole of the driving sprocket 420 can rotate freely around a driving shaft 415 of the motor 410. A plurality of inner and outer friction plates are superimposed in groups to increase the friction. A friction plate pressure plate 480 is fixed to the driving sprocket 420 via a faster 470, and the inner and outer friction plates are pressed by a bead screw 460. By adjusting the bead screw 470, the output torque of the power transmission system 400 can be easily controlled. Finally, a lock nut 450 is used for locking the assembly together to prevent a change in torque due to loosing. The motor 410 drives the pulley system 600 to move back and forth through the inner friction plate 440, the outer friction plate 430, the driving sprocket 420, the chain 4010, the redirecting sprocket 490 and the connecting piece 650 mounted on the chain 4010.

The mechanism of the entire system operates as follows:
a) in an initial state, the pulley 610 is set in its original position, a plug end (not shown) of the head mounted VR display 700 is fixed on the machine 50 frame, and a cable 710 attached to and suspending the head mounted VR display 700 passes through the pulley 610. After the cable 710 is released, the PC host 290 controls the power transmission system 400 to move, which drives the pulley 600 forward until the position limit switch 520 is triggered. Once triggered the position limit switch 520 disconnects the circuit and stops the motor 410 from running.
b) When the pulley 610 moves, the cable 710 is released through the pulley 610 allowing the head mounted VR display 700 to lower due to gravity. As a result, the head mounted VR display 700 is lowered to the position desired by a player.
c) Through a reverse movement of the cable 710, the PC host 290 controls the power transmission system 400 to drive the pulley system 600 in a reverse direction to pull the cable 710 through the pulley 610 in this way, the head mounted VR display 700 is retracted until the home limit switch 510 is triggered to disconnect the circuit, so as to stop the movement.

During the foregoing processes mentioned above, when the movement of the head mounted VR display 700 or the cable 710 is stopped accidentally, the inner friction plate 440 and outer friction plate 430 within the power transmission device 400 slip against each other, which helps unload the excess stress, thus protecting the cable 710 attached to the head mounted VR display 700, and preventing the cable 710 from breaking. If the cable 710 cannot be extended or retracted to a desired position within a certain period of time, a program will be automatically triggered to make the PC host 290 to issue an alarm, so as to warn a background operator that an abnormal situation has occurred.

If the PC host 290 cannot control the system properly due to an issue such as a power failure, a backup power source may be included in the system to power the motor 410 to retract the head mounted VR display 700 to its original position and then power off the system to prevent property damages caused by un-retracted head mounted VR display during a sudden power failure.

A main purpose of the present embodiment is to achieve unattended operation of VR game machines so as to maximize the display effect of VR games. The object of the present embodiment is to meet the requirements of easy transportation, easy installation, easy operation, easy maintenance, and easy display.

The new external device technology employed by the present embodiment adopts a folding combination mode, which divides the large-screen VR integrated game machine 50 (the equipment) into two parts, namely, an upper assembly 100 and a lower assembly 200. The upper assembly 100 is mainly responsible for protecting, retracting and supporting the VR head mounted display cover 170; while the lower assembly 200 is mainly responsible for accommodating the core components of the equipment, including the PC host 290, the speaker (audio device) 270, the liquid crystal display 2012, as well as the power supply and data transmission lines, and the like. The upper assembly 100 and lower assembly 200 can be separated from each other, and a failure of one of the components can be directly repaired or replaced, which does not require on-site maintenance and upgrade, thereby ensuring continuous equipment operation.

Although the embodiments of the present invention have been shown and described in this disclosure, it will be understood by a person skilled in the art that various changes and modifications can be made to these embodiments without departing from the principle and spirit of the present utility model. The scope of the present utility model is thus defined by the appended claims and their equivalents.

The invention claimed is:

1. A stationary large-screen VR integrated game machine, comprising
   a) an upper assembly 100 disposed on, above and moveably attached to a top portion of a lower assembly 200, the upper assembly functioning to store and protect a VR display unit for mounting on the head of a user, the VR display unit mechanically lowered due to gravity and mechanically retracted into the upper assembly 100,
   b) a VR head mounted display retracting device 150 connected to an interior of the upper assembly 100, the VR head mounted display retracting device 150 comprising
      i) an installation protection bracket 300, wherein the installation protection bracket 300 comprises a motor mounting base 310 and a redirecting sprocket mounting base 320 with an outer wall of the motor mounting base 310 connected with a protection cover 330, an inner wall of the protection cover 330 is movably connected to an outer wall of the motor mounting base 310 and an outer wall of the redirecting sprocket mounting base 320,
      ii) a power transmission system 400 disposed within the installation protection bracket 300,
      iii) an electrical control system 500, wherein the electrical control system 500 is mechanically connected to an outer wall of the installation protection bracket 300 and is electrically connected to the power transmission system 400, and
      iv) a pulley system 600 connected to the power transmission system 400, for delivering and retracting the VR head mounted display.

2. The large-screen VR integrated game machine of claim 1 wherein,
   a. the upper assembly 100 comprises an upper assembly casing 110, a lower surface of the upper assembly casing 110 connected with an upper assembly folding device 120, a side of the upper assembly folding device 120 spaced from the upper assembly casing 110 is connected with an upper assembly flip plate 130 with a front surface of the upper assembly folding device 120 connected with a folding device access door 140,
   b. the VR head mounted display retracting device 150 is connected to an interior of the upper assembly casing 110, an upper surface of the upper assembly casing 110 is connected with a retracting device access door 160, and one end of the upper assembly casing 110 is spaced from the upper assembly folding device 120 and is connected with a head mounted display protection cover 170,
   c. a lower surface of the head mounted display protection cover 170 is connected to an ultraviolet disinfection light 180, a lower surface of the upper assembly flip plate 130 is connected with the lower assembly 200 and the head mounted display protection cover 170 and the VR head mounted display retracting device 150 are connected together via a fastener and further fixedly connected to the upper assembly flip plate 130 via a hinge.

3. The large-screen VR integrated game machine of claim 1, wherein:
   a. the lower assembly 200 comprises a lower assembly casing 210, an outer wall of the lower assembly casing 210 having an external power supply socket 220 and a leakage protection circuit breaker 230 attached thereto, the external power supply and socket 220 disposed on a front surface of the leakage protection circuit breaker 230,
   b. the outer wall of the lower assembly casing 210 is connected to a folding device operation switch 240 that is disposed on a rear surface of the leakage protection circuit breaker 230 and is provided with an external network port 250, the outer wall on a first side of the lower assembly casing 210 is movably connected with a power supply board protection door 260 disposed adjacent to the external power supply socket 220,
   c. an audio device 270 is fixed connected to an interior of the lower assembly casing 210 and the outer wall of the lower assembly casing 210 is movably connected to a lower assembly access door 280
   d. a PC host 290 is fixedly connected to a top portion of an inner wall of the lower assembly casing 210, an upper surface of the lower assembly casing 210 is fixedly connected with a cooling fan 2010 and the outer wall of the lower assembly casing 210 is provided with a VR control handle access port 2011,
   e. a liquid crystal display 2012 is movably connected to an interior of the lower assembly casing 210, a touch screen 2013 is fixedly connected to the outer wall on the left side of the liquid crystal display 2012, a display installation protection frame 2014 is fixedly connected to the outer wall of the left side of the lower assembly casing 210, a decorative light set 2015 is fixedly connected to the outer wall of the left side of the lower assembly casing 210, the decorative light set 2015 disposed below the display installation protection frame 2014, a lower surface of the lower assembly casing 210 having a set of wheels 2016 attached thereto.

4. The large-screen VR integrated game machine of claim 1 wherein the power transmission system 400 comprises a motor 410 with a driving sprocket 420 connected to one end of an output shaft 415 of the motor 410, an inner wall of the driving sprocket 420 movably connected with an inner friction plate 440 and an outer friction plate 430, a lock nut 450 is movably connected to an interior of the outer friction plate 430, a bead screw 460 is movably connected to an outer wall of the outer friction plate 430, the driving sprocket 420 is connected to a friction plate pressure 480 through a fastener 470, a chain 4010 is movably connected to an outer wall of the driving sprocket 420, and a redirecting sprocket 490 is movably connected to an interior of the chain 410.

5. The large-screen VR integrated game machine of claim 1 wherein the electrical control system 500 comprises a home limit switch 510, an outer wall of the home limit switch 510 fixedly connected to an outer wall of the motor mounting base 310 and an outer wall of the redirecting sprocket mounting base 320 is fixedly connected with a position limit switch 520.

6. The large-screen VR integrated game machine of claim 1 wherein the pulley system 600 comprises a linear bearing block set 630, an outer wall of the linear bearing block set 630 connected with a bearing mounting base 620, a guide shaft 640 is connected to an outer wall of the bearing mounting base 620, an outer wall of the guide shaft 640 movably connected with a pulley 610, an outer wall of the linear bearing block set 630 is connected with a connecting piece 650 and an outer wall of the connecting piece 650 is movably connected with an outer wall of the chain 410.

7. A large-screen VR integrated game machine, comprising
   a) an upper assembly 100 disposed on and moveably attached to a top portion of a lower assembly 200,
   b) a VR head mounted display retracting device 150 connected to an interior of the upper assembly 100, the VR head mounted display retracting device 150 comprising
      i) an installation protection bracket 300,
      ii) a power transmission system 400 disposed within the installation protection bracket 300,
      iii) an electrical control system 500, wherein the electrical control system 500 is mechanically connected to an outer wall of the installation protection bracket 300 and is electrically connected to the power transmission system 400, and
      iv) a pulley system 600 connected to the power transmission system 400, for delivering and retracting a VR head mounted display,
   wherein the electrical control system 500 comprises a home limit switch 510, an outer wall of the home limit switch 510 fixedly connected to an outer wall of the motor mounting base 310 and an outer wall of the redirecting sprocket mounting base 320 is fixedly connected with a position limit switch 520.

8. The large-screen VR integrated game machine of claim 7 wherein,
   a. the upper assembly 100 comprises an upper assembly casing 110, a lower surface of the upper assembly casing 110 connected with an upper assembly folding device 120, a side of the upper assembly folding device 120 spaced from the upper assembly casing 110 is connected with an upper assembly flip plate 130 with a front surface of the upper assembly folding device 120 connected with a folding device access door 140,
   b. the VR head mounted display retracting device 150 is connected to an interior of the upper assembly casing 110, an upper surface of the upper assembly casing 110 is connected with a retracting device access door 160, and one end of the upper assembly casing 110 is spaced from the upper assembly folding device 120 and is connected with a head mounted display protection cover 170,
   c. a lower surface of the head mounted display protection cover 170 is connected to an ultraviolet disinfection light 180, a lower surface of the upper assembly flip plate 130 is connected with the lower assembly 200 and the head mounted display protection cover 170 and the VR head mounted display retracting device 150 are connected together via a fastener and further fixedly connected to the upper assembly flip plate 130 via a hinge.

9. The large-screen VR integrated game machine of claim 7, wherein:
   a. the lower assembly 200 comprises a lower assembly casing 210, an outer wall of the lower assembly casing 210 having an external power supply socket 220 and a leakage protection circuit breaker 230 attached thereto, the external power supply and socket 220 disposed on a front surface of the leakage protection circuit breaker 230,
   b. the outer wall of the lower assembly casing 210 is connected to a folding device operation switch 240 that is disposed on a rear surface of the leakage protection circuit breaker 230 and is provided with an external network port 250, the outer wall on a first side of the lower assembly casing 210 is movably connected with a power supply board protection door 260 disposed adjacent to the external power supply socket 220,
   c. an audio device 270 is fixed connected to an interior of the lower assembly casing 210 and the outer wall of the lower assembly casing 210 is movably connected to a lower assembly access door 280,
   d. a PC host 290 is fixedly connected to a top portion of an inner wall of the lower assembly casing 210, an upper surface of the lower assembly casing 210 is fixedly connected with a cooling fan 2010 and the outer wall of the lower assembly casing 210 is provided with a VR control handle access port 2011,
   e. a liquid crystal display 2012 is movably connected to an interior of the lower assembly casing 210, a touch screen 2013 is fixedly connected to the outer wall on the left side of the liquid crystal display 2012, a display installation protection frame 2014 is fixedly connected to the outer wall of the left side of the lower assembly casing 210, a decorative light set 2015 is fixedly connected to the outer wall of the left side of the lower assembly casing 210, the decorative light set 2015 disposed below the display installation protection frame 2014, a lower surface of the lower assembly casing 210 having a set of wheels 2016 attached thereto.

10. The large-screen VR integrated game machine of claim 7 wherein the installation protection bracket 300 comprises a motor mounting base 310 and a redirecting sprocket mounting base 320 with an outer wall of the motor mounting base 310 connected with a protection cover 330, an inner wall of the protection cover 330 is movably connected to an outer wall of the motor mounting base 310 and an outer wall of the redirecting sprocket mounting base 320.

11. The large-screen VR integrated game machine of claim 7 wherein the power transmission system 400 comprises a motor 410 with a driving sprocket 420 connected to one end of an output shaft 415 of the motor 410, an inner wall of the driving sprocket 420 movably connected with an inner friction plate 440 and an outer friction plate 430, a lock nut 450 is movably connected to an interior of the outer friction plate 430, a bead screw 460 is movably connected to an outer wall of the outer friction plate 430, the driving sprocket 420 is connected to a friction plate pressure 480 through a fastener 470, a chain 4010 is movably connected to an outer wall of the driving sprocket 420, and a redirecting sprocket 490 is movably connected to an interior of the chain 410.

12. The large-screen VR integrated game machine of claim 7 wherein the pulley system 600 comprises a linear bearing block set 630, an outer wall of the linear bearing block set 630 connected with a bearing mounting base 620, a guide shaft 640 is connected to an outer wall of the bearing mounting base 620, an outer wall of the guide shaft 640 movably connected with a pulley 610, an outer wall of the linear bearing block set 630 is connected with a connecting piece 650 and an outer wall of the connecting piece 650 is movably connected with an outer wall of the chain 410.

* * * * *